(12) United States Patent
Krivan et al.

(10) Patent No.: US 7,790,672 B2
(45) Date of Patent: Sep. 7, 2010

(54) METHOD OF USING LECTINS FOR PREVENTION AND TREATMENT OF ORAL AND ALIMENTARY TRACT DISORDERS

(75) Inventors: Howard C. Krivan, Carson City, NV (US); Richard C. Potter, Stevensville, MT (US); Michael J. Oldham, Orange, CA (US)

(73) Assignee: Legere Pharmaceuticals, Inc., Carson City, NV (US)

( * ) Notice: Subject to any disclaimer, the term of this patent is extended or adjusted under 35 U.S.C. 154(b) by 671 days.

(21) Appl. No.: 11/413,826

(22) Filed: Apr. 28, 2006

(65) Prior Publication Data

US 2006/0194718 A1 Aug. 31, 2006

Related U.S. Application Data

(60) Continuation of application No. 10/654,104, filed on Sep. 3, 2003, now abandoned, which is a division of application No. 10/097,409, filed on Mar. 15, 2002, now abandoned, which is a continuation-in-part of application No. 10/038,645, filed on Jan. 8, 2002, now abandoned, which is a continuation of application No. 08/861,596, filed on May 22, 1997, now abandoned, which is a continuation of application No. 08/640,693, filed on May 1, 1996, now abandoned, which is a continuation of application No. 08/385,306, filed on Feb. 7, 1995, now abandoned.

(51) Int. Cl.
*A61K 39/00* (2006.01)
*A61K 39/38* (2006.01)
*A61K 45/00* (2006.01)
*A61K 38/00* (2006.01)
*A61K 38/16* (2006.01)

(52) U.S. Cl. .............................. 514/2; 514/8; 514/925; 514/926; 514/927; 514/928; 424/184.1; 424/278.1; 424/279.1

(58) Field of Classification Search .................. None
See application file for complete search history.

(56) References Cited

OTHER PUBLICATIONS

Valkonen et al, FEMS Immunology and Medical Microbiology, 1993, 7:29-38.*
Neumann et al, Scandinavian J.Gastroenterology, 2007, 42:791-798.*
Baczako et al, J. Pathology, 1995, 176:77-86.*

* cited by examiner

*Primary Examiner*—N. M Minnifield
(74) *Attorney, Agent, or Firm*—Shook Hardy & Bacon LLP

(57) ABSTRACT

Infectious diseases caused by pathogenic microorganisms resident in the alimentary tract of humans and animals can be prevented and treated by administering to the alimentary tract of the human or animal an effective amount of a composition containing at least one lectin capable of binding to an infective microorganism and diminishing its infective capability of the microorganism. The lectin is administered dispensed in a pharmaceutically acceptable non-toxic vehicle. Peptic ulcer disease caused by infection with *H. pylori* can be treated by oral administration of lectins that bind to the pathogen. A beneficial ecology of *H. pylori* can be maintained in infected patients by chronic oral administration of lectins that bind to the pathogen.

13 Claims, No Drawings

METHOD OF USING LECTINS FOR PREVENTION AND TREATMENT OF ORAL AND ALIMENTARY TRACT DISORDERS

CROSS-REFERENCE TO RELATED APPLICATIONS

This application is a continuation and claims the benefit of priority to U.S. patent application Ser. No. 10/654,104, filed on Sep. 3, 2003, abandoned, which is a divisional of U.S. application Ser. No. 10/097,409, filed Mar. 15, 2002, abandoned, which is a continuation-in-part of application Ser. No. 10/038,645, filed Jan. 8, 2002, abandoned, which is a continuation of application Ser. No. 08/861,596, filed May 22, 1997, abandoned, which is a continuation of application Ser. No. 08/640,693, filed May 1, 1996, abandoned, which is a continuation of application Ser. No. 08/385,306, filed Feb. 7, 1995, abandoned.

STATEMENT REGARDING FEDERALLY SPONSORED RESEARCH OR DEVELOPMENT

Not applicable.

TECHNICAL FIELD

This invention relates generally to methods of prevention and treatment of oral and alimentary diseases and more particularly to the use of oral administration of lectins for prophylaxis against and treatment of oral and alimentary diseases and disorders.

BACKGROUND OF THE INVENTION

Numerous diseases of humans and animals are caused by microorganisms that colonize the internal nasal passages and the alimentary tract, which comprises the mouth, pharynx, and gastrointestinal tract. While many of these diseases are acute conditions caused by bacteria that are self-limiting or treatable by conventional antibiotic therapy, others are caused by microorganisms that tend to establish chronic infections that cause continuing symptoms and are often difficult to treat with antibiotics.

Gastritis and duodenal peptic ulcers (commonly described as peptic ulcer disease) involve an inflammation and/or erosion of the mucosal lining of the stomach or duodenum. These pathological conditions were thought for many years to be the result of hypersecretion of stomach acid caused by either genetic predisposition, stress, or diet, or a combination of these factors. This belief led to a medical treatment regime including drugs of various classes (antacids, histamine $H^2$ receptor antagonists, $H^+$ inhibitors, $K^+$ inhibitors, proton pump inhibitors, ATPase inhibitors and the like) that neutralize the excess acid or inhibit its secretion. While such therapy has had generally good results, it is often necessary to continue the treatment for the patient's entire lifespan because discontinuing treatment usually results in relapse of the disease. Recently, it has been established that the pathogen *Helicobacter pylori*, a spiral bacterium, is a factor in the development of gastritis and duodenal peptic ulcers. This bacterium has been found to colonize the gastric epithelium and to cause damage to the epithelial cells which results in a gastritis that predisposes the organ to the formation of ulcers. *H. pylori* has also been linked to development of gastric adenocarcinoma and B cell lymphoma in the stomach. *H. pylori*'s in vivo role in gastritis and peptic ulcers and its association with the second leading cause of cancer deaths in the world, gastric cancer (second only to lung cancer), make it one of the world's most prevalent and significant pathogens.

Indeed, in recent years it has come to be recognized that *H. pylori* infection of the stomach can result in a broad spectrum of debilitating disease outcomes, including gastritis, non-ulcer dyspepsia, peptic ulcer disease, and gastric cancers. For example, in the United States about 50% of the population may be infected with this organism, and currently about 25 million patients suffer from peptic ulcer disease. Each year there are 500,000 to 850,000 new cases and more than one million ulcer-related hospitalizations. On a global scale, the frequency of *H. pylori* infection is much higher and kills 7 million people each year.

In recent years, treatment of *H. pylori* infection with antimicrobial therapy has been found to heal peptic ulcers, eliminate chronic gastritis and dyspepsia, and may lead to regression of gastric cancer. However, there is currently no therapy that is 100% effective. Although numerous antibiotics have activity against *H. pylori* in vitro, therapy with a single antibiotic is generally ineffective in clinical practice. Successful treatment often requires combination therapy consisting of 3-4 drugs given for periods of 10-14 days. Treatment failure occurs frequently, and second-line treatments with new antibiotic regimens are common. Perhaps the single most important factor influencing treatment is the emergence of antibiotic-resistant strains of *H. pylori*. Consequently, antibiotic therapy may be subject to certain limitations in the future.

*Cryptosporidium parvum* is a pathogenic intestinal protozoan with worldwide distribution that is a frequent cause of both endemic and epidemic diarrheal illness. This illness is particularly devastating in immunocompromised individuals, producing diarrhea with profuse watery stools accompanied by cramping, abdominal pain, nausea, vomiting, malaise and low grade fever that increases over months and years. Currently, there are no preventative therapies and anti-infective drugs are of limited efficacy.

Periodontal disease is a major reason for tooth loss in adults. Microbioloyically, periodontal disease is a polymicrobic problem involving anaerobic bacteria: *Treponema denticola, Bacteroides forsythus, Actinobacillus actinomycetemcomitans, Campylobacter rectus, Prevotella intermedia*, and *Porphyromonas gingivalis*, as well as others. This disease is more prominent in patients with dental implants, since the natural gum never fully adheres to the implant (false tooth) providing space for bacterial attachment and growth. Currently, treatments include more frequent tooth cleaning by dental hygienists, more frequent brushing with special dentifrices, and more frequent use of mouthwashes. While all current treatments decrease the probability and severity of periodontal disease, there is still a significant amount of tooth loss and none of the current approaches deals effectively with microbial attachment to the tooth or the buccal mucosa (gum).

*Streptococcus pyogenes* is an organism that can cause an acute pharyngitis with suppurative consequences caused by spread to other organs (otitis media, abscesses, meningitis, and the like) and/or non-suppurative consequences caused by toxins produced by some strains (scarlet fever). It is generally controllable with penicillins, but other methods of treatment are desirable because allergic reactions to penicillin are not uncommon.

Accordingly, a need has continued to exist for improved methods of treating and preventing disease of the oral cavity and alimentary tract caused by pathogenic microorganisms. In particular, a need has continued to exist for safe and effective methods of treating gastro-intestinal disorders due to infection with *H. pylori*.

SUMMARY OF THE INVENTION

This need for more convenient and effective therapy and prophylaxis of diseases of the nasal cavity and alimentary tract has now been alleviated by the method of this invention, according to which one or more lectins capable of binding to the surface of pathogenic microorganisms of the alimentary tract or nasal cavity or to the tissues that line the alimentary tract and nasal cavity themselves are administered orally or nasally to a patient infected with such pathogens or to a person in danger of being exposed to such pathogens. It is also according to the invention to administer a lectin orally in a dosage form derived from fractionation of a natural source of lectin, as, for example, administration of WGA lectin in a fraction derived from a source of WGA such as wheat germ.

Accordingly, it is an object of the invention to provide an improved method for treating peptic ulcer disease.

A further object is to provide a method of prophylaxis for peptic ulcer disease.

A further object is to provide a method of prophylaxis for gastritis.

A further object is to provide a method of treatment for gastritis.

A further object is to provide a method for prophylaxis against *Helicobacter pylori*.

A further object is to provide a method of treatment for infections caused by *Helicobacter pylori*.

A further object is to provide a method for prophylaxis against *Cryptosporidium parvum*.

A further object is to provide a method of treatment for infections caused by *Cryptosporidium parvum*.

A further object is to provide a method for prophylaxis against *Streptococcus pyogenes*.

A further object is to provide a method of treatment for infections caused by *Streptococcus pyogenes*.

A further object is to provide a method of prophylaxis for periodontal disease.

A further object is to provide a method of treating periodontal disease.

A further object is to provide a method for binding pathogenic microorganisms in the alimentary tract.

A further object is to provide a method for binding target cells in the alimentary tract.

A further object is to provide vehicles for delivering lectins to the alimentary tract.

Other objects of the invention will become apparent from the following detailed description.

DETAILED DESCRIPTION OF THE INVENTION

Lectins are carbohydrate-binding proteins of nonimmune origin that agglutinate cells or precipitate polysaccharides or glycoconjugates, i.e., proteins or lipids conjugated to oligo- or polysaccharides. They are widely distributed, and have been isolated from both plant and animal sources. Their reactions with living cells are based on their ability to bind with antibody-like specificity to particular arrangements of the sugar residues that make up oligo- or polysaccharides.

The surface of eucaryotic cells contains very numerous molecules of glycoproteins and glycolipids. Such glycoconjugates are found in the plasma membranes of cells of multicellular animals, including mammals and humans, as well as on the surfaces of single-celled eucaryotic organisms. Similarly, the cell walls of bacteria and the envelopes and capsids of viruses contain structural polysaccharides and/or glycoproteins. The carbohydrate moieties of these molecules which are displayed on the cell surfaces exhibit great variety in composition and structure that serves to distinguish the types of cells and to serve as a signal to other cells or materials which come into contact with the cell. For, example, variation in the carbohydrate moieties of glycoproteins in the plasma membrane of red blood cells serves as the basis for the conventional blood typing classification. When lectins recognize and bind to certain carbohydrate moieties they may serve to cross-link and agglutinate the cells bearing the binding groups, a property that earns for them the alternate name of agglutinins. Furthermore, because the same sort of carbohydrate moieties often serve as attachment points for pathogens to bind to target cells and invade them, lectins may block infection of target cells by blocking the sites used by pathogens as recognition markers. The same type of specific binding occurs between sperm and egg in conception, and can be blocked by lectins. The binding ability of lectins may be very specific for certain mono- or oligosaccharides, allowing lectins to be used as a powerful tool for investigating the oligosaccharide epitopes on the surface of organisms or cells. Lectins can distinguish between blood cells of specific blood type, malignant from normal cells, and among species and genera of organisms. While glycoproteins, glycolipids, and bacterial cell walls and capsules are believed to be the main lectin-binding locations on the surfaces of cells, it is not excluded that carbohydrate moieties derived from other molecules or cellular structures may be displayed on the cell surface or that other lectin-binding structures may be targets for the lectins used in the method of this invention.

Current medical uses of lectins include distinguishing erythrocytes of different blood types (blood typing). More recently, lectins have been used ex-vivo in depleting T cells of patients undergoing bone marrow transplantation.

Among the microorganisms that are bound by certain lectins are infectious organisms such as bacteria, protozoa, fungi, and viruses. Lectins may be used to identify such microorganisms in vitro and are also capable of binding to them in vivo, thereby preventing them from infecting living cells. Human disease-causing organisms (and the diseases caused by them) that can be bound by lectins include numerous sexually transmitted diseases as described in copending U.S. patent application Ser. No. 08/317,599, filed Oct. 3, 1994, as well as *Helicobacter pylori, Cryptosporidium parvum, Treponema denticola; Bacteroides forsythus, Actinobacillus actinomycetemcomitans, Streptococcus pyogenes, Campylobacter rectus, Prevotella intermedia*, and *Porphyromonas gingivalis*, as well as others. Other infections and diseases in which the portal of entry or initial attachment is nasal, oral, or in the alimentary tract are also capable of being prevented by administration of lectins according to this invention.

According to the invention, a dose of lectins effective to bind and agglutinate pathogenic microorganisms and/or block the recognition sites on target cells is administered to the nose, mouth, or alimentary tract prophylactically or as therapy. Because of the specificity of lectins for certain microorganisms, it is preferred to administer a mixture of lectins chosen for their properties of agglutinating specific pathogens.

A representative listing of lectins, the abbreviations by which they are referred to, and their sources is given in Table 1.

TABLE 1

Lectins and Abbreviations

| Lectin | Source |
|---|---|
| AAnA | *Anguilla anguilla* (Eel serum) |
| AAP | *Aaptos papillata* (sponge) |
| AaurA | *Aleuria aurantia* (Orange peel fungus) |
| ABA | *Agaricus bisporus* (Mushroom) |
| ABrA | *Amphicarpanea bracteata* (hog-peanut) |
| ACG | *Achatina granulata* (snail) |
| AL | *Hippaestrum* hybrid (Amaryllis bulbs) |
| APA | *Abrus precatorius* (Jequirity bean) |
| AS | *Avena sativa* (oat) |
| BDA | *Bryonia dioica* (white bryony) |
| BIL | *Birgus latro* (Cocoknut crab) |
| BOO | *Boltenia ovipera* (Tunicate) |
| BPA | *Bauhinia purpurea alba* (camel's foot tree) |
| BRS | *Brachypodium sylvaticum* (brome grass) |
| CA | *Coichicum autumnale* (meadow saffron) |
| CAA | *Caragana arborescens* (Siberian pea tree) |
| CAA | *Capsicum annuum* (hot herb) |
| CCA | *Cancer antennarius* (California crab) |
| CMA | *Chelidonium majus* (greater celandine) |
| ConA | *Concanavalia ensiformis* (Jack bean) |
| CPA | *Cicer arietinum* (chick pea) |
| CSA | *Cytisus scoparius* (Scotch broom) |
| CUM | *Cucurbita maxima* (winter squash) |
| CUP | *Curcubita pepo* (squash) |
| CYSE | *Cytisus sessilifolius* (shrub) |
| DAC | *Daucus carota* (carrot) |
| DAI | *Datura innoxia* (harmless jimson weed) |
| DBA | *Dolichos biflorus* (horse gram) |
| DSA | *Datura stramonium* (Jimson weed, Thorn apple) |
| ECA | *Erythrina crystagalli* (Coral tree) |
| ECorA | *Erythrina coralidendron* (Coral tree) |
| EEA | *Euonymus europaeus* (spindle tree) |
| GNA | *Galanthus nivalis* (Snowdrop bulb) |
| GRT | *Gracilaria tikvahiae* (Ceylon moss) |
| GSA-1/GSA-1 I (GS-II) | *Griffonia simplicifolia* (African legume isolectin) |
| HAA | *Helix aspersa* (Garden snail) |
| HEB | *Hevea brasilliensis* (rubber tree) |
| HEL | *Helix hortensis* (Snail) |
| HOV | *Hordeum vulgare* (barley) |
| HPA | *Helix pomatia* (Roman or edible snail) |
| JAC (Jacalin) | *Artocarpus integrifolia* (jackfruit) |
| LAA | *Laburnum alpinum* |
| LBA | *Phaseolus lunatis* (also limensis) (Lima bean) |
| LCA (LcH) | *Lens culinaris* (lentil) |
| LEA | *Lycopersicon esculentum* (Tomato) |
| LFA | *Liniax flavus* (garden slug) |
| LIP | *Limulus polyphemus* (Horseshoe crab) |
| LOA | *Lathyrus oderatus* (Sweet pea) |
| LTA (LOTUS) | *Lotus tetragonolobus* (Asparagus pea) |
| LUA | *Luffia actangula* (gourd) |
| LYE | *Lycopersicon esculentum* (tomato) |
| MAA | *Maackia amurensis* (maackia) |
| MIH | *Mangifera indica* (Mango) |
| MPA | *Maclura pomifera* (Osage orange) |
| NPL (NPA) | *Narcissus pseudonarcissus* (daffodil) |
| OTL | *Oryza sativa* (rice) |
| PAA | *Persea americana* (Avocado) |
| PAD | *Papaver dubium* (doubtful poppy) |
| PHA (PHA-L) | *Phaseolis vulgaris* (Red kidney bean) |
| PIG | *Pila globosa* (Snail) |
| PNA | *Arachis hypogaea* (Peanut) |
| PSA | *Pisum sativum* (Pea) |
| PSV | *Psathyrella velutina* (mushroom) |
| PWA | *Phytolacca americana* (pokeweed) |
| PTAgalactose | *Psophocarpus tetagonolobus* (winged bean) |
| PTAgalNac | *Psophocarpus tetagonolobus* (winged bean) |
| QUR | *Quercus rubra* (English or red oak) |
| RCA-I/RCA-II | *Ricinus communis* (Castor bean) |
| RPA | *Robinia pseudoaccacia* (black locust) |
| SBA | *Glycine max* (Soybean) |
| SCL | *Secale cereale* (rye) |
| SEI | *Sesamum indicum* (sesame) |
| SJA | *Sophora japonica* (Japanese pagoda tree) |

TABLE 1-continued

Lectins and Abbreviations

| Lectin | Source |
|---|---|
| SNA | *Sambuccus nigra* (elderberry) |
| SOA | *Solanum alatum* (winged nightshade) |
| SOM | *Solanum melongena* (eggplant) |
| STA | *Solanium tuberosum* (Potato) |
| TICD | *Tilia cordata* (basswood) |
| TKA | *Trichosanthes kinlowii* (China gourd) |
| TL | *Tulipa* sp. (tulip) |
| TMT | *Tomentine* (seaweed Codium tomentosum) |
| UDA | *Urtica diolca* (Stinging nettle) |
| UEA-I/UEA-I1 | *Ulex europaeus* (Gorse or Furz seeds) |
| VAA | *Viscum album* (European mistletoe) |
| VFA | *Vicia faba* (Fava bean) |
| VGA | *Vicia graminea* |
| VisalbCBA | *Viscum album* (mistletoe) |
| VRA | *Vigna radiata* (mung bean) |
| VSA | *Vicia sativa* |
| VVA | *Vicia villosa* (Hairy vetch) |
| WFA | *Wisteria floribunda* (Japanese wisteria) |
| WGA | *Triticum vulgaris* (Wheat germ) |
| suc-WGA(sWGA) | Succinyl WGA |

The choice of lectins for prophylaxis or treatment of a particular infection is determined by the lectin—binding properties of the pathogenic microorganism, which is in turn determined by the composition of the particular oligosaccharide residues of the glycoproteins and glycolipids found on the external surface of the pathogen.

For example, *Cryptosporidium parvum* oocysts are bound by lectins that bind to N-acetyl-D-glucosamine residues on their surfaces (Liovo, J., et al., *J. Infectious Diseases* 1993, 167, pp. 1477-1480.). Such lectins include UEA-II and Tomentine. A lectin from *Codium fragile* (a type of seaweed) specific for Nacetyl-D-glucosamine also agglutinates *Cryptosporidium parvum* oocysts. Such lectins include BDA, ConA, BDA, SBA, GSA-I, GSA-II, HAA, HPA, LAA, LBA, RCA-II, SNA, SJA, and WGA.

A number of lectins can bind to oral mucosa and block potential attachment sites of pathogenic bacteria. Such lectins include DBA, LTA, RCA, SBA, UEA, and WGA.

While the lectins discussed above and the organisms against which they are effective are representative of useful lectins according to the invention, it is to be understood that other lectins may be discovered which are active in the binding and agglutination of nasal, oral and alimentary tract pathogens.

The selection of specific lectins to be administered will depend on the diseases sought to be prevented. It is preferred to administer a lectin or mixture of lectins, selected for best agglutinative efficacy against the specific pathogen or pathogens responsible for the disease. It is also according to the invention to prevent or treat infectious diseases caused by pathogenic microorganisms that colonize the surface of the mucosa lining the alimentary canal by administering a dose of lectins capable of binding to the receptors on the mucosal tissue to which the organisms bind in their attack on the mucosal cells. When the receptors on the cells are blocked, the initial binding of the microorganism to the cell, which in many cases is necessary for it to exert its pathological activity, is blocked, and the disease is prevented.

The lectins may be administered in any fluid or vehicle suitable for nasal or oral administration of pharmaceutical compounds. Inasmuch as lectins are generally dispersible in aqueous vehicles, the practitioner may choose a vehicle from among a broad range of conventional pharmaceutically acceptable non-toxic vehicles. Thus, mouthwash, chewing gum, pills, tablets (chewable and non-chewable), caplets, toothpaste, dental floss, nasal sprays, and the like, may be formulated in which the selected lectins are dispersed in a non-toxic vehicle for nasal, oral and alimentary tract administration.

A preferred embodiment of the invention comprises oral administration of lectins capable of binding to *Helicobacter pylori* in order to prevent infection by that organism or to treat gastritis or duodenal ulcers related to infection with *H. pylori*. The treatment comprises administration to a patient infected with *H. pylori* an amount of a lectin capable of binding to *H. pylori* effective to diminish the infective capability of the microorganism. The exact dose will depend on the strength of binding between the lectin and *H. pylori*, i.e., on the binding constant of the interaction between the lectin and the receptors for the lectin on the surface of the microorganism, and on the number of surface receptors on the microorganism that have to be saturated with lectin in order to produce an effective decrease in the infective capability of the microorganism. The effective dose will also depend on the severity and extent of the infection, i.e., on the number of microorganisms present and the bioavailability of the lectin to interact with these microorganisms and incapacitate their ability to bind to and injure the cells of the gastric and duodenal mucosa. Accordingly, while the practitioner can gain some guidance as to an effective dose from the experimental determination of the binding effectiveness of a given lectin for *H. pylori*, it must be expected that determination of an effective dose will involve some experimentation of the type that is entirely conventional in the development of pharmaceutical treatment of infectious diseases.

The practice of the invention will be illustrated by the following example, which is intended to be illustrative and is not to be construed as limiting the scope of the appended claims.

EXAMPLE 1

This example illustrates the binding of various lectins to *Helicobacter pylori*.

The efficacy of binding of several lectins to *H. pylori* was investigated in vitro by the following procedures.

Growth of Bacteria: Toxigenic (ATCC 49503) and non-toxigenic (ATCC 43504, type strain) strains of *H. pylori* were obtained from the American Type Culture Collection (10801 University Boulevard, Manassas, Va. 20110-2209. *H. pylori* were grown under microaerophilic conditions at 37° C. for 4-5 days on blood agar plates containing 5% sheep blood. The bacteria were harvested with 0.01 M sodium phosphate buffer (pH 7.2) containing 0.15 M NaCl (PBS), washed twice and suspended to a final optical density of 0.15 in sodium bicarbonate buffer, pH 9.5, before being used.

Lectin Binding Assay: Biotinylated lectins were reconstituted in phosphate buffered saline (10 mM sodium phosphate-150 mM NaCl, pH 7.2) and stored in a freezer at 70° C. until used. Washed *H. pylori* were suspended in sodium bicarbonate buffer (pH 9.5). Microtiter plates washed with 95% ethanol and dried were coated with bacteria by adding 200 µl of the suspension to each well and incubating overnight at room temperature. Wells coated with bacteria were washed three times with sodium acetate buffered saline, pH 4.0, containing 0.5% Tween 20 detergent (ABS-T), and the appropriate biotinylated lectin was added at the test concentration. Lectins defrosted at room temperature were diluted in each buffer, and 100 µl of various lectins was added to bacteria-coated wells at a final concentration of 50 µg/ml. After incubation in a humid chamber at room temperature for 2 hours, the wells were emptied and washed five times with ABS-T. Bound biotinylated lectin was detected by the addition of streptavidin-alkaline phosphatase (10 ng/µl) followed after two hours by washing three times with ABS-T and addition of 100 µl of freshly prepared p-nitrophenyl phosphate (1 mg/ml) in 0.1 M Tris buffer-0.15 M NaCl. Color production was quantitated by spectrophotometry at 405 nm.

The results of the lectin-binding tests are summarized in Table 2 for the toxigenic strain (ATCC 49503) and in Table 3 for the non-toxigenic strain (ATCC 43504). The tables present the following data:

1. Maximum rate of color production in the *Lectin Binding Assay* (mOD/minute). This provides an indication of the maximum number of lectin binding sites.

2. Concentration of lectin which gives rise to 50% maximum rate of color production (micrograms/milliliter). This provides an indication of the affinity of the binding sites.

3. Ratio (quotient) of maximum rate of lectin production to concentration of lectin at ½ the maximum rate.

In Tables 2 and 3 the first column indicates the lectin which was tested in the binding experiment, the numbers in the second and third columns are averages of the results of three replications of the lectin binding experiment with the indicated lectin, and the numbers in the third column represent the quotient of the average values given in the second and third columns.

TABLE 2

REACTIVITY OF PLANT LECTINS WITH *H. PYLORI* (ATCC 49503)

| Lectin | Max. rate (mOD/min) | $[Lectin]_{1/2\,Max}$ (µg/ml) | Quotient |
|---|---|---|---|
| sWGA | 188.37 | 0.63 | 299.00 |
| MPA | 358.63 | 1.56 | 229.89 |
| ConA | 273.92 | 1.54 | 177.87 |
| LEA | 295.81 | 2.06 | 143.60 |
| Jacalin | 332.96 | 3.26 | 102.13 |
| VVA | 529.35 | 4.80 | 110.28 |
| VFA | 518.79 | 5.45 | 95.19 |
| WGA | 3540.40 | 7.84 | 451.58 |
| CPA | 564.80 | 9.44 | 59.83 |
| WFA | 572.63 | 10.10 | 56.70 |
| LCA | 468.49 | 10.30 | 45.48 |
| GNA | 334.76 | 10.60 | 31.58 |
| NPA | 517.84 | 13.39 | 38.67 |
| TKA | 300.04 | 14.79 | 20.29 |
| STA | 300.16 | 14.82 | 20.25 |
| PSA | 185.44 | 14.93 | 12.42 |
| CSA | 655.79 | 15.88 | 41.30 |
| Lotus | 495.91 | 16.01 | 30.98 |
| MAA | 354.12 | 20.52 | 17.26 |
| LAA | 354.11 | 20.52 | 17.26 |
| SBA | 476.64 | 26.67 | 17.87 |
| BPA | 395.65 | 33.54 | 11.80 |
| LBA | 1425.53 | 34.05 | 41.87 |
| DSA | 241.72 | 55.01 | 4.39 |
| RPA | 281.01 | 71.77 | 3.92 |
| ABA | 125.44 | 115.82 | 1.08 |
| HAA | 467.62 | 147.15 | 3.18 |

TABLE 3

REACTIVITY OF PLANT LECTINS WITH *H. PYLORI* (ATCC 43504)

| Lectin | Max. rate (mOD/min) | $[Lectin]_{1/2\,Max}$ (µg/ml) | Quotient |
|---|---|---|---|
| sWGA | 93.56 | 0.43 | 217.58 |
| ConA | 177.18 | 1.06 | 167.15 |
| LCA | 377.36 | 2.11 | 178.84 |

TABLE 3-continued

REACTIVITY OF PLANT LECTINS WITH *H. PYLORI* (ATCC 43504)

| Lectin | Max. rate (mOD/min) | [Lectin]$_{1/2\ Max}$ (μg/ml) | Quotient |
|---|---|---|---|
| MPA | 411.39 | 2.12 | 194.05 |
| LEA | 418.61 | 2.60 | 161.00 |
| VFA | 240.90 | 2.84 | 84.82 |
| WGA | 869.79 | 3.03 | 287.06 |
| WFA | 660.37 | 3.15 | 209.64 |
| STA | 191.47 | 3.24 | 59.10 |
| LBA | 540.72 | 3.81 | 141.92 |
| VVA | 740.44 | 6.22 | 119.04 |
| NPA | 356.14 | 9.96 | 35.76 |
| CSA | 649.81 | 13.67 | 47.54 |
| Lotus | 468.49 | 27.91 | 16.79 |
| GNA | 298.92 | 17.63 | 16.96 |
| MAA | 392.32 | 22.61 | 17.35 |
| LAA | 390.01 | 25.70 | 15.18 |
| Lotus | 468.49 | 27.91 | 16.79 |
| SBA | 573.86 | 31.04 | 18.49 |
| ABA | 83.43 | 38.87 | 2.15 |
| TKA | 657.29 | 54.91 | 11.97 |
| BPA | 596.88 | 55.30 | 10.79 |
| JAC | 337.65 | 66.96 | 5.04 |
| RPA | 658.70 | 84.81 | 7.77 |
| DSA | 315.7 | 113.25 | 2.79 |
| HAA | 685.63 | 324.93 | 2.11 |

In these assays, the numbers representing the concentration of lectin which gives rise to 50% maximum rate of color production provide a measure of the ability of each lectin to bind to *H. pylori* and thereby of its potential usefulness in prophylaxis against infections by *H. pylori* and treatment of such infections. The smaller values represent a greater affinity and hence a greater usefulness in prophylaxis and therapy. In practice, those lectins having a value of [lectin] ½ max greater than about 50 are not expected to be useful as agents against *H. pylori*. Those lectins having a value of [lectin] ½ max less than about 8.00 have especially good binding properties with regard to *H. pylori* and are expected to be particularly useful in prophylaxis and therapy. Such preferred lectins include sWGA, MPA, ConA, LEA, Jacalin, VVA, VFA and WGA.

For therapy of disease caused by infection with *H. pylori* it is preferred to use those lectins that will bind preferentially to that pathogenic organism. It is known that *H. pylori* expresses certain glycoconjugates on its exterior surface that can be targets for binding by lectins. In particular, *H. pylori* exhibits sialic acid (N-acetylneuraminic acid, NeuAc) and 9-O-acetylneuraminic acid as well as N-acetylglucosamine on its external surface. Accordingly, lectins that have a high binding affinity for sialic acids or N-acetylglucosamine are preferred for treatment of *H. pylori* infections. Preferred lectins that bind to sialic acids include sWGA, WGA, SNA, PIG, MAA, LIP, LFA, HEL1, GRT, CAA, BOO, BIL, and ACG. Preferred lectins that bind to N-acetylglucosamine include sWGA, WGA, TICD, STA, SOM, SOA, SEI, SCL, SAA, QUR, PSV, PAD, OTL, LYE, LUA, LUA, NOVI GS-II, DAC, DAI, DSA, CMA, CYSE, CUP, CUM, CAA, BRS, and AAP. Especially preferred lectins are those that are present in commonly consumed foods, and derivatives of those lectins, e.g., sWGA, WGA, SNA, GRT, SEI, SCJJ, OTL, LYE, LUA, HOV, and DAC. WGA lectin is a highly preferred lectin because it binds strongly to *H. pylori* and is an abundant dietary lectin. Accordingly, WGA is readily available and is relatively inexpensive. The lectin sWGA (succinylated WGA) is also preferred because of its high binding affinity for *H. pylori* however it is somewhat more expensive because of the extra processing required to form the derivative.

The amount of lectin to be administered is an amount effective to reduce the symptoms caused by the presence of *H. pylori* in the gastrointestinal tract. This can be determined in an individual case by the conventional tests for the presence of *H. pylori*, as discussed below. The dose will also be adjusted depending on the affinity of a particular lectin for *H. pylori*. Those lectins having a relatively low affinity for *H. pylori* will require a relatively large dose of lectin; those having a greater affinity for the pathogenic microorganism will require a relatively smaller dose. The determination of an effective dose is within the capability of the skilled practitioner taught by this specification without undue experimentation. In particular for WGA the effective dose will range from about 0.1 milligrams to about 250 milligrams, preferably from about 0.7 milligrams to about 100 milligrams, and more preferably from about 1.0 milligram to about 10 milligrams. The dose may be administered one or more times a day as required.

The lectin may be administered in a non-toxic pharmaceutical excipient. Any conventional excipient suitable for oral administration can be used as indicated above. It is preferred to administer the lectin in a food or food concentrate. For example, it is preferred to administer WGA lectin in wheat germ because it naturally occurs in wheat germ and wheat germ is a readily available dietary supplement. For example, as discussed below, a typical defatted wheat germ may contain an effective amount of WGA in a dose comprising about 20 grams. Such a dose can be easily measured and consumed by a patient. In certain circumstances, it may be preferable to administer WGA in a non-defatted wheat germ vehicle, because the activity of WGA is substantially greater therein than in defatted wheat germ, and may range up to more than 100 to 500 times the activity in defatted wheat germ. The activity of a lectin in a dosage form or sample, e.g., the activity of WGA in a wheat germ, is a measure of how effective a given weight or volume of the dosage form is with respect to inhibition of a microorganism, e.g., *H. pylori*. A dosage form having greater activity than another dosage form of equivalent weight or volume is generally referred to as a more "concentrated" dosage form, because it contains more lectin per unit weight or volume or at least more of the active form of the lectin, e.g., WGA lectin, per unit weight or volume. Accordingly, in this application the term "concentrated dosage form" indicates a dosage form that has a relatively high activity per unit volume or at least a higher activity per unit volume than a comparison dosage form that is not concentrated. The activity of WGA with respect to inhibition of *H. pylori* in a particular sample of wheat germ may be determined by any conventional procedure, for example, by the hemagglutinin titer as described below. The skilled practitioner will select a wheat germ having a suitable activity of WGA according to the method chosen to administer the lectin to a selected patient or group of patients. In some cases, it may be desirable to administer the desired effective dose of WGA lectin in a dosage form of relatively low activity to be consumed with meals as a food or food concentrate as indicated above. In other cases, it may be desirable to administer the lectin in a highly active or highly concentrated dosage form as a dose of one or more tablets, capsules, or the like.

Consequently, it may be desirable to concentrate the natural product in which a lectin occurs in order to prepare a dosage form that is more concentrated and may be taken in a smaller physical amount. For example, native or natural wheat germ is a product derived from the milling of wheat and separating the germ from the other products of the milling.

Wheat germ is produced and marketed in many forms, for example, raw wheat germ, heat-stabilized wheat germ, partially or substantially completely defatted wheat germ, and the like. The activity of the WGA lectin in the wheat germ may be affected by the processing employed to produce the various forms of wheat germ. For example, because WGA is a protein it may be at least partially denatured by one or more of the processing steps, e.g., heating, used in preparing a particular form of wheat germ. Such denaturation will reduce the activity of the WGA in the particular form of wheat germ. Accordingly, the activity of WGA in a particular form or sample of wheat germ may not be entirely determined by the concentration of the WGA protein in the sample. However, the activity can be measured directly as indicated above and exemplified below. In general, it is preferred to select, for the practice of the invention, a wheat germ that has experienced a minimum of degradation and inactivation of the active WGA lectin contained therein. Furthermore, it has been found that these conventional and commercially available wheat germs are heterogeneous products that can be separated into fractions by a fractionation procedure. Certain, fractions have been found to have higher concentrations and/or activity of WGA lectin than others. Any conventional wheat germ, such as those enumerated above, can be fractionated to yield a fraction containing a higher concentration and/or activity of WGA than the original unfractionated material. A preliminarily fractionated wheat germ can also be subjected to further fractionation according to the invention to yield a highly concentrated material containing a high concentration or activity of WGA. It is according to the invention to administer the effective dose of lectins according to the invention in such a more concentrated or more active form prepared by fractionating wheat germ and selecting a fraction containing a higher activity or concentration of lectin than the original material. Such fractionation may advantageously be preceded by any of a variety of dry or wet milling techniques, including pin milling, hammer milling, roller milling, Wiley milling, jet milling, colloid milling, and the like, and combinations thereof. The fractionation of the selected wheat germ starting material can be suitably effected by wet or dry means, including air classification, wet sieving, dry sieving, solvent extraction, dissolution and reprecipitation, dissolution and anion exchange chromatography, dissolution and affinity chromatography, centrifugation, ultracentrifugation, ultrafiltration, diafiltration, and the like, and combinations thereof. Any conventional milling and/or fractionation procedure is suitable for fractionating a wheat germ according to the invention. It is also intended that a multiplicity of such milling and fractionation steps may be used to prepare a fraction having increased lectin concentration and/or activity.

It is also according to the invention to treat *H. pylori* infection by administration of a plurality of lectins.

EXAMPLE 2

This example illustrates the treatment of gastritis due to infection with *H. pylori* by oral administration of WGA lectin.

A group of seven patients was selected from among patients presenting in a gastroenterology practice for enrollment in the test. Criteria for enrollment were:

Age 18-65 years

Active symoptomatic *H. pylori*-associated peptic ulcer disease documented by endoscopy of the upper gastrointestinal tract Active *H. pylori* infection documented by endoscopic biopsies and diagnosed by the CLOtest and urea breath test Any patients exhibiting severe acute medical illnesses or wheat allergy, as well as any patients using aspirin, non-steroidal anti-inflammatory drugs (NSAIDS) or other ulcerogenic drugs were excluded.

All enrolled patients were given an entrance physical examination. In addition to assessment for inclusion and exclusion criteria, each patient was evaluated by baseline CBC, blood chemistry panel, *H. pylori* serology, and urea breath test prior to therapy. All entered patients were treated for 4 weeks with WGA lectin at selected dosages. Each patient was given a take-home diary to report symptoms on a weekly basis. At the end of 4-6 weeks, each patient was evaluated by upper endoscopy with biopsy for histopathology and detection of the presence of *H. pylori* by the CLOTEST. A urea breath test, a CBC and chemistry panel was also performed. All tests were performed by standard acceptable methodologies approved by the Food and Drug Administration (FDA).

The efficacy of the treatment was assessed primarily by healing as indicated by endoscopic criteria, i.e., absence of *H. pylori* in the antrum on histopathologic examination. The efficacy of treatment was also assessed by a marked decrease in the urea breath test values.

The CLOtest® (Tri-Med Specialties, Inc., Draper, Utah) is a colorimetric test that enables a gastroenterologist rapidly to determine the presence of *H. pylori* in a gastric biopsy. In use, a biopsy sample is applied to a card substrate containing a diagnostic reagent and the presence of *H. pylori* is indicated by the development of a red color around the biopsy, produced by the action of the urease enzyme present in the *H. pylori* organisms. The test is highly specific for the presence of *H. pylori*.

The urea breath test is a standard non-invasive test for diagnosing a stomach infection with *H. pylori*. The test is performed by orally administering a dose of radiocarbon-labeled urea. If *H. pylori* is present in the stomach, the urease enzyme produced by the bacteria breaks down the urea into ammonia and carbon dioxide. The radiolabeled carbon dioxide is absorbed through the lining of the stomach into the bloodstream and is expelled in the breath. Typically breath samples are taken 6, 12, and 20 minutes after administration of the test compound. If radioactivity levels in the breath rise by a predetermined amount, the presence of *H. pylori* in the stomach is diagnosed.

According to the test protocol, the patients were given a dosage of WGA lectin, a lectin which had been determined in in vitro studies, (e.g., such as described in Example 1 above) to bind to *H. pylori*. The WGA was administered as a natural ingredient in defatted wheat germ, which is a rich source of this lectin. The experimental doses were one or two tablespoons of defatted wheat germ (about 10 or 20 grams, respectively), mixed in a suitable drink (water, tea, etc.) and taken either once a day at bedtime or twice a day. The dose and schedule was varied for each patient according to the test results to achieve an effective treatment.

A summary of the test and its results is given in Table 4.

TABLE 4

Effect of WGA Lectin and Dosage on Patients Afflicted with *H. pylori*

| Patient | Dosage (TBSP) | Time Line (wks) | Symptom Rating | Urea Breath Test (% $^{14}CO_2$) |
|---|---|---|---|---|
| 1 | 0 | 0 | 7 | 33.4 |
|   | 1 qd | 2.5 | 5 | 45.5 |
|   | 1 bid | 6 | 2 | 27.7 |
|   | 1 bid | 8 | 1 | 28.1 |
| 2 | 0 | 0 | 8 | 17.6 |
|   | 1 bid | 6 | 6 | 5.7 |
|   | 1 bid | 9 | 0 | 8.5 |
|   | 1 bid | 13 | 0 | 4.1 |
|   | 1 bid | 19 | 1 | 4.8 |
|   | 2 bid | 25 | 5 | 11.2 |
|   | 2 bid | 34 | 0 | 6.6 |
|   | 2 bid | 40 | 0 | 4.7 |
| 3 | 0 | 0 | 8 | 3.1 |
|   | 1 bid | 6 | 2 | 1.4 |
| 4 | 0 | 0 | 10 | 22.3 |
|   | 1 bid | 7 | 0 | 54.9 |
|   | 1 bid | 14 | 0 | 31.5 |
|   | 1 bid | 20 | 0 | 19.7 |
|   | 1 bid | 29 | 0 | 14.6 |
|   | 1 bid | 36 | 0 | 22.5 |
| 5 | 0 | 0 | 10 | 30.0 |
|   | 2 bid | 6 | 3 | 28.7 |
|   | 1 bid | 13 | 4 | 15.5 |
|   | 2 qd | 22 | 4 | 20.1 |
|   | 2 qd | 28 | 0 | 8.9 |
|   | 2 qd | 36 | 1 | 8.3 |
| 6 | 0 | 0 | 10 | 67.4 |
|   | 2 qd | 4 | 2 | 54.5 |
|   | 2 qd | 8 | 0 | 39.7 |
|   | 2 qd | 40 | 0 | 36.3 |
| 7 | 0 | 0 | 10 | 27.5 |
|   | 2 qd | 6 | 0 | 16.4 |
|   | 2 qd | 12 | 0 | 10.1 |

[a] Dosage taken at time indicated wherein qd = once before bedtime; bid = twice a day at morning and night
[b] symptoms, wherein 0 = none and 10 = maximum complaints
[c] UBT = urea breath test where values are expressed as percent CO2 produced from *H. pylori* urease activity In the test reported above, defatted wheat germ was the source of lectin (Viobin #9, Viobin U.S.A., Monticello, Ill.) and used as the vehicle in the test. The amount of WGA lectin contained in the dose administered was about 1.0, milligram. The skilled practitioner will recognize that, because wheat germ from any variety of wheat is a rich source of WGA lectin, as pointed out above, any wheat germ product, defatted or non-defatted, from any manufacturer is suitable as a source of such lectin and/or a vehicle for administering the lectin, provided that the manufacturer's wheat germ product meets conventional standards of purity, wholesomeness, and the like. Consequently, all such wheat germ products are included within the scope of the invention.

All patients enrolled in this pilot study initially complained of gastritis and tested positive for *H. pylori* infection. Gastroenterology physicians graded symptoms by assigning scores on a scale of 0 to 10, with most severe symptoms given a score of 10. Within 1-2 weeks of treatment with WGA lectin, symptoms declined markedly and continued to decline over time with continued therapy. These results were also consistent with decreased urea breath test (UBT) values, indicating a reduction in *H. pylori* infectivity (Table 4).

Assessment of symptom scores and UBT values early on in the trial indicated a dosage of two tablespoons of defatted wheat germ containing WGA taken once before bedtime (2 qd) was optimal. Continued therapy with WGA lectin according to the invention presented with major improvement in pain-related quality of life and absence of *H. pylori*-associated disease without intervention with antibiotics or other anti-acid medicines.

The results of the test indicate that oral administration of WGA lectin appears to be safe and have widespread efficacy in *H. pylori*-associated disease. Therapy with WGA lectin did not appear to be therapeutic for patients that complained of gastritis and tested negative for *H. pylori* infection (data not shown), indicating that WGA lectin has a specific mechanism of action against this gastric pathogen.

Although continued therapy appears to arrest infection and improve patient outcomes, the organism was not eradicated. Low-level UBT values in all patients treated were sufficient to indicate a remaining presence of *H. pylori*. This discovery can have a practical application, however, in light of recent data that suggest that eradication of *H. pylori* may increase the prevalence of gastroesophageal reflux disease (GERD) and its complications (i.e., Barret's and esophageal neoplasia), at least in some patients. The issue of a "protective" role for *H. pylori* has been further magnified by several other recent investigations. Consequently, it is becoming clear that *H. pylori* may be related to GERD in that its absence, at least in some circumstances, may very well result in lowering the threshold for development of other gastric diseases. Accordingly, in some patients it can be desirable to maintain a controlled population of *H. pylori* in the gastrointestinal tract. Therefore, it is also according to the invention to administer lectins such as WGA in order to control the population of *H. pylori* in the gastrointestinal tract of a patient and thereby prevent further development of *H. pylori*-associated disease, yet maintain *H. pylori* ecology sufficient to serve as a protective factor with respect to GERD and its complications.

The defatted wheat germ used as a vehicle in the test of efficacy of WGA lectin is a well-known source of WGA lectin. WGA lectin is a naturally occurring material in wheat germ, and the amount of this active agent in a particular sample of wheat germ, defatted or non-defatted can be determined by standard assays.

For example, the amount of lectin in a given sample of wheat germ or similar material can be evaluated by the following example of an extraction and analysis procedure.

Lectin Extraction of Wheat Germ: One kilogram of pulverized defatted wheat germ (defatted by cold solvent extraction and milled to a tine powder) is extracted by rocking with 2 liters of 50 mM sodium acetate buffer, pH 4.5, at room temperature. After 4 hours, an additional 0.5 liter of extraction buffer is added and extraction is continued overnight for 24 hours. The extracted slurry is centrifuged at 6,700×g for 1 hour. The supernatant extract was decanted through Whatman 40 filter paper using a vacuum pump. The filtrate extract is then brought to 40% saturation with (NH4)2SO4, allowed to mix overnight at room temperature, and centrifuged at 6,700× g. Salt pellets are suspended in 50 mN sodium acetate buffer, mixed, and dialyzed in phosphate buffered saline (PBS) overnight at 4° C. (molecular weight (MW) cut-off 12,000-14,000). The dialysate is filtered through a Whatman 40 filter and tested for lectin activity by the hemagglutination assay.

Lectin Hemagglutination Assay: Rabbit erythrocytes are washed three times in 10 volumes of PBS (pH 7.2) and diluted to a 2.5% suspension. Twofold serial dilutions of wheat germ agglutinin (WGA) lectin, defatted wheat germ extract or other lectins (50 pl) are performed with PBS in V-bottom microtiter plates (Dynatech), and 50 pl of fresh washed erythrocytes is added to each well. The plates are gently tapped, and the erythrocytes are allowed to settle at room temperature. Titers are expressed as the reciprocal of the highest dilution of lectin in which hemagglutination is visible macroscopically.

The range of hemagglutination titers typically found from extracted defatted wheat germ is 8 to 128, depending on the final extract concentration; the range of hemagglutinin titers for raw wheat germ may range from 16,384 to 65,536.

The invention having now been fully described, it should be understood that it may be embodied in other specific forms or variations without departing from its spirit or essential characteristics. Accordingly, the embodiments described above are to be considered in all respects as illustrative and not restrictive, the scope of the invention being indicated by the appended claims rather than by the foregoing description, and all changes which come within the meaning and range of equivalency of the claims are intended to be embraced therein.

We claim:

1. A method of treating a patient afflicted with an *H. pylori* infection of the gastrointestinal tract, the method comprising:
   orally administering to said patient a dose of a lectin-containing compound that is effective to diminish symptoms caused by the infection.

2. The method of claim 1 wherein a lectin that is contained in the lectin-containing compound is capable of binding to sialic acid.

3. The method of claim 2 wherein said lectin is selected from the group consisting of sWGA, WGA, SNA, PIG, MAA, LIP, LFA, HEL, GRT, CAA, BOO, BIL, and ACG.

4. The method of claim 2 wherein said lectin is selected from the group consisting of sWGA and WGA.

5. The method of claim 1 wherein a lectin that is contained in the lectin-containing compound is capable of binding to N-acetylglucosamine.

6. The method of claim 5 wherein said lectin is selected from the group consisting of sWGA, WGA, TICD, STA, SOM, SOA, SEI, SCL, SAA, QUR, PSV, PAD, OTL, LYE, LUA, LUA, HOV, GS-II, DAC, DAI, DSA, CMA, CYSE, CUP, CUM, CAA, BRS, and AAP.

7. The method of claim 6 wherein said lectin is selected from the group consisting of sWGA and WGA.

8. The method of claim 6 wherein said lectin is WGA.

9. The method of claim 8 wherein the amount of WGA administered is from about 0.1 milligrams to about 250 milligrams.

10. The method of claim 8 wherein the amount of WGA administered is from about 0.7 milligrams to about 100 milligrams.

11. The method of claim 8 wherein the amount of WGA administered is from about 1.0 milligrams to about 10 milligrams.

12. A method of treating a patient afflicted with an *H. pylori* infection of the gastrointestinal tract, the method comprising:
    orally administering to said patient a dose of a lectin-containing compound that is effective to diminish symptoms caused by the *H. pylori* infection, wherein a lectin included in the lectin-containing compound is not bound to an antigen when the lectin-containing compound is administered.

13. A method of treating a patient afflicted with an *H. pylori* infection of the gastrointestinal tract, the method comprising:
    orally administering to said patient an amount of wheat germ agglutinin, which includes a dose of a lectin, wherein the dose is effective to diminish symptoms caused by the *H. pylori* infection.

* * * * *